US00PP25149P3

(12) United States Plant Patent
Korlipara

(10) Patent No.: US PP25,149 P3
(45) Date of Patent: Dec. 2, 2014

(54) *ECHINACEA* PLANT NAMED 'METEOR YELLOW'

(50) Latin Name: ***Echinacea* hybrid**
Varietal Denomination: Meteor Yellow

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 132 days.

(21) Appl. No.: 13/815,547

(22) Filed: Mar. 8, 2013

(65) Prior Publication Data

US 2014/0259246 P1 Sep. 11, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Meteor Yellow' characterized by enlarged disc florets forming an anemone-type inflorescence, yellow ray florets and yellow orange disc florets, ray florets which are held horizontally, a short, mounding habit with excellent stem count, and excellent vigor.

1 Drawing Sheet

Botanical denomination: *Echinacea* hybrid.
Variety designation: 'Meteor Yellow'.

BACKGROUND OF THE INVENTION

The present invention relates to a new and distinct cultivar of *Echinacea* and given the cultivar name 'Meteor Yellow'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Secret Joy' (U.S. Plant Pat. No. 23,627), the new cultivar is much shorter and has darker yellow inflorescences.

Compared to *Echinacea* 'Pineapple Sundae', the new cultivar is shorter and has smaller cones and ray florets which are held more horizontally.

This new *Echinacea* cultivar is distinguished by:

1. enlarged disc florets forming an anemone-type inflorescence,
2. yellow ray florets and yellow orange disc florets,
3. ray florets which are held mostly horizontally,
4. a short, mounding habit with excellent stem count, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Meteor Yellow' growing in the garden in full sun in early July in Canby, Oreg.

DETAILED PLANT DESCRIPTION

The following is a detailed description of the new *Echinacea* cultivar based on observations of three-year-old specimens growing in the trial beds in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to about 50 cm wide and 53 cm tall to top of inflorescences.
*Form.*—Basal clump, with about 20 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 3 inflorescences per stem.
*Size.*—To 47 cm tall to a terminal inflorescence and 5 mm wide at base.
*Internode length.*—0.5 to 8 cm.
*Surface texture.*—Strigose.
*Color.*—Yellow Green 151A.

Leaf (basal):

*Type.*—Simple.

*Shape.*—Ovate to lanceolate.

*Arrangement.*—Basal.

*Blade size.*—Grows to 10 cm long and 6 cm wide.

*Margins.*—Coarsely serrate.

*Apex.*—Acute.

*Base.*—Attenuate.

*Surface texture.*—Strigose on both sides.

*Venation.*—Pinnate, with 3 main veins from the base, Yellow Green 145D on both sides.

*Color.*—Topside, Green 137B, bottom side closest to Yellow Green 147B.

*Petiole description.*—Grows to 14 cm long and 3 mm wide above the clasp, sparsely strigose, Yellow Green 145B.

Leaf (stem):

*Type.*—Simple.

*Shape.*—Lanceolate.

*Arrangement.*—Alternate.

*Blade size.*—Grows to 12 cm long and 4 cm wide.

*Margins.*—Coarsely serrate.

*Apex.*—Acuminate.

*Base.*—Attenuate.

*Surface texture.*—Strigose on both sides.

*Venation.*—Pinnate, with 3 main veins from the base, Yellow Green 145D on both sides.

*Color.*—Topside Green 137B, bottom side closest to Yellow Green 147B.

*Petiole description.*—On all but upper leaves, clasping, grows to 4.5 cm long and 3 mm wide above the clasp, strigose, both sides Yellow Green 147B on sides and 145C in center.

Inflorescence:

*Type.*—Composite on terminal stalked heads.

*Number of flowering stems from the ground.*—About 20.

*Flowering stem.*—Grows to 47 cm tall from the base of the plant to the terminal inflorescence and can grow to 9 cm long from the top stem leaf to the base of an inflorescence; branched with 1 to 3 inflorescences per stem; diameter growing to 7 mm wide near the inflorescence; strigose; Yellow Green 151A.

*Size.*—Grows to 7.5 cm wide and 4.5 cm deep as disc enlarges.

*Form.*—Ray florets held slightly reflexed, mature disc is conic.

*Immature inflorescence.*—Grows to 2.5 cm wide and 2 cm deep, ray florets held at a 55 degree angle from the horizontal and rolled up so only the back color shows, Yellow 10C, disc color Yellow Green 144A.

*Ray florets.*—Without pistil or stamen, about 28 in number, grow to 37 mm long and 7 mm wide, oblanceolate with the tip two-toothed to two-lobed (lobes to 7 mm long and 3 mm wide), tips acute, entire margins, base attenuate, glabrous on both sides; top side between Yellow Orange 18A when first fully open changing to Yellow Orange 15D when disc florets are fully open, bottom side Yellow Orange 18D.

*Disc.*—Flat becoming conic, growing to 25 mm deep and 45 mm wide with maturity, Yellow Green 144A when disc florets are closed to Yellow Orange 22B when disc florets are open.

*Disc florets.*—To about 300 in number, each with 1 pistil and 4 stamen, grow to 20 mm long and 7 mm wide, each with one persistent, very stiff linear bract (11 mm long with 2 mm Orange 25B at apex blending to 3 mm Yellow Green 145D to White 155A at base); corollas to 18 mm long and 7 mm wide, tubular at base (to 5 mm long and 1.5 mm wide, Yellow Green 147C) then oblanceolate with tip usually 2 lobed (1 side lobe linear, cut to the tube, and reflexed, to 15 mm long and 1 mm wide; main lobe 1 mm long and 3 mm wide, oblanceolate with 2 terminal lobes grow to 5 mm deep and 1.5 mm wide), margin entire, tips acute, base attenuate, glabrous on both sides, topside Yellow Orange 23A, bottom side Yellow Orange 19B; pistil 7 mm long, ovary 2 mm long, White NN155A, style 5 mm long White 155A, 2-branched stigma spreading, Yellow 4D; stamen 4 mm long, filaments 3 mm long, threadlike, White 155A, anthers 1 mm long, Greyed Purple N186A, no pollen, male sterile.

*Phyllaries.*—In 4 leafy series, area grows to 33 mm wide and 10 mm deep, lobes lanceolate in shape, reflexed, grow to 18 mm long and 4 mm wide, both sides Yellow Green 147B, margins strigose, tip acute, strigose.

*Receptacle.*—Grows to 12 mm wide and 13 mm deep, White NN155B.

*Bloom period.*—July through October in Canby, Oreg.

*Fragrance.*—Sweet, floral.

*Lastingness.*—Each inflorescence lasts about two weeks in Canby, Oreg.

*Seeds.*—None seen.

*Fertility.*—Poor.

Disease and pests: No pests or diseases have been observed on plants grown under commercial conditions in Canby, Oreg. No resistances are known.

I claim:

1. A new and distinct *Echinacea* plant as herein illustrated and described.

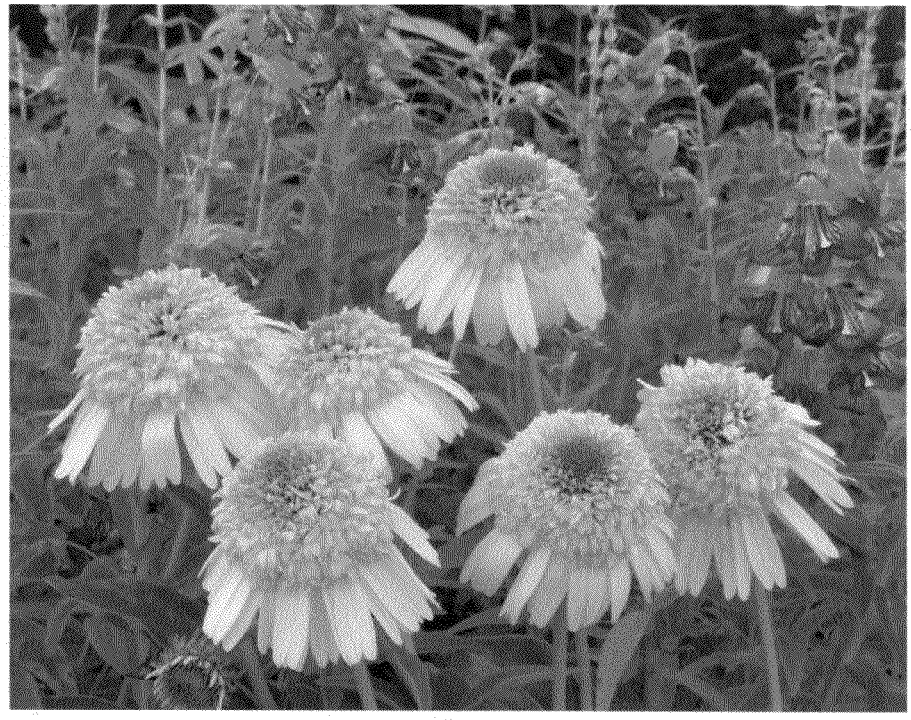

* * * * *